United States Patent [19]

Johnson

[11] 4,018,914

[45] Apr. 19, 1977

[54] PARTURITION INDUCEMENT
[75] Inventor: Edwin Samuel Johnson, Antioch, Ill.
[73] Assignee: Abbott Laboratories, North Chicago, Ill.
[22] Filed: Nov. 13, 1975
[21] Appl. No.: 631,773
[52] U.S. Cl. .............................................. 424/177
[51] Int. Cl.$^2$ ....................................... A61K 37/02
[58] Field of Search ................................... 424/177
[56] References Cited
UNITED STATES PATENTS
3,914,412  10/1975  Gendrich et al. .................. 424/177

OTHER PUBLICATIONS

Southern—The Prostaglandins (Clinical Applications in Human Reproduction) (1972) p. 4.

*Primary Examiner*—Sam Rosen
*Attorney, Agent, or Firm*—Paul D. Burgauer; Robert L. Niblack

[57] ABSTRACT

Certain nonapeptides have been found to induce parturition in warm-blooded animals if administered within the last phase of pregnancy.

4 Claims, No Drawings

PARTURITION INDUCEMENT

DETAILED DESCRIPTION OF THE INVENTION

In many animals, including humans, pregnancies often extend beyond the calculated time of delivery. In many instances when this occurs, it is associated with considerable discomfort and, in isolated cases, the fetus will grow beyond the size that enables smooth or normal delivery thereof, endangering the life of mother and/or fetus.

Gynecologists and veterinaries have long known this problem and have used a variety of physical or chemical means to terminate pregnancies successfully at the time calculated for normal delivery or slightly before. Among the chemical parturition inducing means, oxytocin has taken a leading role, although it is expensive and has to be given intravenously or by infusion.

It has now been found that the compounds described in U.S. Pat. No. 3,914,412 and their homologs orally can be used in a similar fashion. This invention is therefore directed to the process of inducing parturition essentially consisting in administering, to a warm-blooded animal within the last 10% of its gestation period, a compound of the formula L-pGlu-L-His-L-Trp-L-Ser-L-Tyr-D-X-L-Leu-L-Arg-L-Pro-NH-alkyl wherein X stands for an aminoacid moiety of the formula —NH—CHR'—CO— and R' stands for a linear or branched alkyl of 1–4 carbons. This compound can be administered orally or parenterally, particularly intramuscularly or subcutaneously. For parenteral administration, a single dose of 0.02 to 1.0 mg/kg administered at the calculated endpoint of pregnancy or within the last 10% of a normal gestation period will produce the desired termination of pregnancy. If oral administration is preferred, a single dose of 2–100 mg/kg will produce the above effect. The indicated, single doses often will be sufficient when administered once; however, they may be repeated 1–2 times a day for several days until parturition takes place.

The compounds used for this purpose are the L-pGlu-L-His-L-Trp-L-Ser-L-Tyr-X-L-Leu-L-Arg-L-Pro-NHR wherein X represents an aminoacid moiety in the D-form of formula —NH—CHR'—CO— with R' representing a linear or branched alkyl chain of 1–4 carbons, and wherein R represents loweralkyl. These compounds induce an estrogen surge when administered in the above fashion which, in turn, produces the desired effect on the uterus that leads to parturition.

In order to illustrate the process of the present invention, reference is made to the following examples which, however, are not meant to limit the invention in any way.

EXAMPLE 1

Pregnant rats with exactly known dates of mating were divided into groups which were treated as shown in the table below. Normal pregnancy in these species last 21.5 days which is exactly what was observed in the control group, receiving 0.5 ml. of a 0.1% bovine serum albumin solution in 0.9% aqueous sodium chloride. The test animals received 20 μ in two equal portions, of L-pGlu-L-His-L-Trp-L-Ser-L-Tyr-D-Leu-L-Leu-L-Arg-L-Pro-NH-ethyl as a 0.04 g/l solution in 0.9% aqueous sodium chloride containing 0.1% bovine serum albumin. In all instances, the subcutaneous injections were given on day 18 of gestation.

Table I

|  | Animals per Group | Day of Parturition | Mean Number of Pups |
| --- | --- | --- | --- |
| Control | 4 | 2 at 22; 2 at 21 | 9.8 |
| Test compound | 3 | 1 at 21; 2 at 20 | 8.7 |

EXAMPLE 2

In a repetition of the procedure of Example 1, the same test was carried out except that the animals were injected on day 19 of gestation. The results are given in Table II.

Table II

|  | Animals per Group | Day of Parturition | Mean Number of Pups |
| --- | --- | --- | --- |
| Control | 4 | 1 at 22; 3 at 21 | 10.0 |
| Test compound | 3 | 3 at 21 | 9.3 |

While the above examples are directed to rats, it will be appreciated by those skilled in the art that the findings with these test animals are directly correlatable to other warm-blooded animals. In all instances, the pups delivered were healthy and indistinguishable from the control animals' pups. Also, the results with half and two times the dose level of example 1 produced essentially the same result as shown in Table I.

The compounds of U.S. Pat. No. 3,914,412 of which the compound used in the above examples is a characteristic species, all produce essentially the same results. These compounds all induce ovulation in animals carrying a mature follicle, and it is therefore fully expected that they all produce the result shown with one member of the very small group of nonapeptides encompassed by the above formula.

Tablets, for oral administration or solutions suitable for parenteral administration are prepared in the same fashion as described in the above identified reference. Also, posology is essentially the same but, of course, the recipient for the treatment according to this invention is a different animal and the treatment has a different purpose. In the current process, parturition is induced where a gestation has essentially gone the full length usually counted for the particular animal species.

I claim:
1. The process of inducing parturition essentially consisting in administering to a warm-blooded animal within the last 10% of its gestation period, an effective amount of a compound of the formula L-pGlu-L-His-L-Trp-L-Ser-L-Tyr-D-X-L-Leu-D-X-L-Leu-L-Arg-L-Pro-NH-alkyl wherein X stands for an aminoacid moiety of the formula —NH—CHR'—CO— and R' stands for a linear or branched alkyl of 1–4 carbons.
2. The process of claim 1 wherein said compound is administered orally at a dose of 2–100 mg/kg.
3. The process of claim 1 wherein said compound is administered parenterally at a dose of 0.02–1.0 mg/kg.
4. The process of claim 1 wherein said R' is isobutyl and said alkyl is ethyl.

* * * * *

UNITED STATES PATENT AND TRADEMARK OFFICE
CERTIFICATE OF CORRECTION

PATENT NO. : 4,018,914
DATED : April 19, 1977
INVENTOR(S) : Edwin Samuel Johnson It is certified that error appears in the above-identified patent and that said Letters Patent are hereby corrected as shown below:

In Claim 1, column 2, line 55, after "-D-X-L-Leu-", delete "D-X-L-Leu-". (This is an erroneous duplication of the term "D-X-L-Leu-".)

Signed and Sealed this

Thirteenth Day of September 1977

[SEAL]

Attest:

RUTH C. MASON
Attesting Officer

LUTRELLE F. PARKER
Acting Commissioner of Patents and Trademarks